(12) United States Patent
Kovatchev

(10) Patent No.: US 10,925,536 B2
(45) Date of Patent: Feb. 23, 2021

(54) SYSTEMS OF CENTRALIZED DATA EXCHANGE FOR MONITORING AND CONTROL OF BLOOD GLUCOSE

(71) Applicant: University of Virginia Patent Foundation, Charlottesville, VA (US)

(72) Inventor: Boris P. Kovatchev, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 405 days.

(21) Appl. No.: 15/109,682

(22) PCT Filed: Jan. 5, 2015

(86) PCT No.: PCT/US2015/010167
§ 371 (c)(1),
(2) Date: Jul. 5, 2016

(87) PCT Pub. No.: WO2015/103543
PCT Pub. Date: Jul. 9, 2015

(65) Prior Publication Data
US 2016/0331310 A1    Nov. 17, 2016

Related U.S. Application Data

(60) Provisional application No. 61/923,361, filed on Jan. 3, 2014.

(51) Int. Cl.
| | | |
|---|---|---|
| *A61B 5/00* | (2006.01) |
| *A61B 5/0402* | (2006.01) |
| *A61B 5/11* | (2006.01) |
| *A61B 5/145* | (2006.01) |
| *G06F 19/00* | (2018.01) |
| *G16H 50/30* | (2018.01) |
| *G16H 40/63* | (2018.01) |
| *A61B 5/021* | (2006.01) |
| *A61M 5/142* | (2006.01) |
| *A61M 5/172* | (2006.01) |
| *A61B 5/0488* | (2006.01) |
| *A61B 5/022* | (2006.01) |
| *A61B 5/024* | (2006.01) |

(52) U.S. Cl.
CPC .......... *A61B 5/4839* (2013.01); *A61B 5/0022* (2013.01); *A61B 5/0024* (2013.01); *A61B 5/021* (2013.01); *A61B 5/0402* (2013.01); *A61B 5/11* (2013.01); *A61B 5/14532* (2013.01); *A61B 5/7275* (2013.01); *A61B 5/746* (2013.01); *A61M 5/142* (2013.01); *A61M 5/14276* (2013.01); *A61M 5/1723* (2013.01); *G06F 19/325* (2013.01); *G06F 19/3418* (2013.01); *G06F 19/3468* (2013.01); *G16H 40/63* (2018.01); *G16H 50/30* (2018.01); *A61B 5/022* (2013.01); *A61B 5/024* (2013.01); *A61B 5/02416* (2013.01); *A61B 5/0488* (2013.01); *A61B 2562/0219* (2013.01); *A61M 2205/3584* (2013.01); *A61M 2205/3592* (2013.01); *A61M 2205/50* (2013.01); *A61M 2205/52* (2013.01); *A61M 2230/005* (2013.01); *A61M 2230/04* (2013.01); *A61M 2230/06* (2013.01); *A61M 2230/201* (2013.01); *A61M 2230/30* (2013.01)

(58) Field of Classification Search
None
See application file for complete search history.

(56) References Cited

U.S. PATENT DOCUMENTS

| | | |
|---|---|---|
| 2004/0102683 A1 | 5/2004 | Khanuja et al. |
| 2011/0124996 A1 | 5/2011 | Reinke et al. |
| 2014/0127729 A1* | 5/2014 | Moran ............ G01N 33/48771 435/14 |

FOREIGN PATENT DOCUMENTS

WO    2012/178134 A2    12/2012

* cited by examiner

*Primary Examiner* — G Steven Vanni
(74) *Attorney, Agent, or Firm* — Buchanan Ingersoll & Rooney PC

(57) ABSTRACT

A flexible system capable of utilizing data from different monitoring techniques and capable of providing assistance to patients with diabetes at several scalable levels, ranging from advice about long-term trends and prognosis to real-time automated closed-loop control (artificial pancreas). These scalable monitoring and treatment strategies are delivered by a unified system called the Diabetes Assistant (DiAs) platform. The system provides a foundation for implementation of various monitoring, advisory, and automated diabetes treatment algorithms or methods. The DiAs recommendations are tailored to the specifics of an individual patient, and to the patient risk assessment at any given moment. A central data exchange node or server collects patient data from individual DiAs devices and provides safety assurance, monitoring, telemedicine and database building for the DiAs system.

30 Claims, 7 Drawing Sheets

SYSTEMS OF CENTRALIZED DATA EXCHANGE FOR MONITORING AND CONTROL OF BLOOD GLUCOSE

CROSS-REFERENCE TO RELATED APPLICATIONS

This application claims priority from U.S. Provisional Application No. 61/923,361 filed Jan. 3, 2014, under 35 U.S.C. § 119 (c) and PCT Article 8

BACKGROUND OF THE INVENTION

Diabetes mellitus (DM), often simply referred to as diabetes, is a group of metabolic diseases characterized by high glucose levels in the blood (i.e. hyperglycemia), either because the body does not produce enough insulin (Type 1 DM or T1DM), or because cells do not respond to the insulin that is produced (Type 2 DM or T2DM). Intensive treatment with insulin and with oral medications to maintain nearly normal levels of glycemia (i.e. euglycemia) markedly reduces chronic complications in both T1DM and T2DM [1,2,3], but may risk symptomatic hypoglycemia and potentially life-threatening severe hypoglycemia. Therefore, hypoglycemia has been identified as the primary barrier to optimal diabetes management [4,5]. People with T1DM and T2DM face a lifelong optimization problem: to maintain strict glycemic control without increasing their risk for hypoglycemia. However, the struggle for close glycemic control could result in large blood glucose (BG) fluctuations over time. This process is influenced by many external factors, including the timing and amount of insulin injected, food eaten, physical activity, etc. In other words, BG fluctuations in diabetes are the measurable result of the interactions of a complex and dynamic biological system, influenced by many internal and external factors.

The optimization of this system depends largely on self-treatment behavior, which has to be informed by glucose monitoring and has to utilize data and technology available in the field. The currently accessible data sources include self-monitoring of blood glucose (SMBG), continuous glucose monitoring (CGM), as well as assessment of symptoms and self-treatment practices. The available treatments include medication (exclusively for T2DM), multiple daily insulin injections (MDI), and insulin pumps (CSII—continuous subcutaneous insulin injection). Currently, these treatments are at various stages of development and clinical acceptance, with SMBG now a routine practice, COM rapidly developing, and emerging integrated systems that combine COM with CSII and pave the way for the artificial pancreas of the near future.

Self-Monitoring of Blood Glucose

Contemporary home BG meters offer convenient means for frequent and accurate BG determinations through SMBG [6,7]. Most meters are capable of storing BG readings (typically over 150 readings) and have interfaces to download these readings into a computing device such a PC. The meters are usually accompanied by software that has capabilities for basic data analysis (e.g. calculation of mean BG, estimates of the average BG over the previous two weeks, percentages in target, hypoglycemic and hyperglycemic zones, etc.), logging of the data, and graphical representations of the BG data (e.g. histograms, pie charts, etc.). In a series of studies we have shown that specific risk analysis of SMBG data could also capture long-term trends towards increased risk for hypoglycemia [8, 9,10], and could identify 24-hour periods of increased risk for hypoglycemia [11,12].

The basics of the risk analysis are presented below. The methods outlined here have been applied to both SMBG and CGM data.

Evaluating Risk for Hypoglycemia and Hyperglycemia: These methods are based on the concept of Risk Analysis of BG data [13], and on the recognition of a specific asymmetry of the BG measurement scale that can be corrected by a mathematical data transformation [14]. The risk analysis steps are as follows:

1. Symmetrization of the BG scale: A nonlinear transformation is applied to the BG measurements scale to map the entire BG range (20 to 600 mg/d, or 1.1 to 33.3 mmol/l) to a symmetric interval. The BG value of 112.5 mg/dl (6.25 mmol/l) is mapped to zero, corresponding to zero risk for hypo- or hyperglycemia. The analytical form of this transformation is $f(BG,\alpha,\beta)=[(\ln (BG))^{\alpha}-\beta]$, $\alpha$, $\beta>0$, where the parameters are estimated as $\alpha=1.084$, $\beta=5.381$, $\gamma=1.509$, if BG is measured in mg/dl and $\alpha=1.026$, $\beta=1.861$, $\gamma=1.794$ if BG is measured in mmol/l [14].

2. Assignment of a risk value to each SMBG reading: We define the quadratic risk function $r(BG)=10f(BG)^2$. The function r(BG) ranges from 0 to 100. Its minimum value is achieved at BG=112.5 mg/dl (a safe euglycemic BG reading), while its maximum is reached at the extreme ends of the BG scale. Thus, r(BG) can be interpreted as a measure of the risk associated with a certain BG level. The left branch of this parabola identifies the risk of hypoglycemia, while the right branch identifies the risk of hyperglycemia.

3. Computing measures of risk for hypoglycemia and glucose variability: Let $x_1, x_2, \ldots x_n$ be a series of n BG readings, and let $rl(BG)=r(BG)$ if $f(BG)<0$ and 0 otherwise; $rh(BG)=r(BG)$ if $f(BG)>0$ and 0 otherwise. Then the Low Blood Glucose Index (LBGI) is computed as:

$$LBGI = \frac{1}{n}\sum_{i=1}^{n} rl(x_i)$$

In other words, the LBGI is a non-negative quantity that increases when the number and/or extent of low BG readings increases. In studies, the LBGI typically accounted for 40-55% of the variance of future significant hypoglycemia in the subsequent 3-6 months [8,9,10], which made it a potent predictor of hypoglycemia based on SMBG. Similarly, we compute the High Blood Glucose Index (HBGI) as follows:

$$HBGI = \frac{1}{n}\sum_{i=1}^{n} rh(x_i)$$

The HBGI is a non-negative quantity that increases when the number and/or extent of high BG readings increases.

Continuous Glucose Monitoring

Since the advent of continuous glucose monitoring technology 10 years ago [15,16,17], which initially had limited performance particularly in the hypoglycemic range [18,19], significant progress has been made towards versatile and reliable CGM devices that not only monitor the entire course of BG day and night, but also provide feedback to the patient, such as alarms when BG reaches preset low or high levels. A number of studies have documented the benefits of continuous glucose monitoring [20,21,22,23] and charted guidelines for clinical use and its future as a precursor to closed-loop control [24,25,26,27]. However, while CGM has the potential to revolutionize the control of diabetes, it also generates data streams that are both voluminous and complex. The utilization of such data requires an understanding of the physical, biochemical, and mathematical principles and properties involved in this new technology. It is important to know that CGM devices measure glucose concentration in a different compartment—the interstitium. Interstitial glucose (IG) fluctuations are related to BG presumably via the diffusion process [28,29,30]. To account for the gradient between BG and IG, CGM devices are calibrated with capillary glucose, which brings the typically lower IG concentration to corresponding BG levels. Successful calibration would adjust the amplitude of IG fluctuations with respect to BG, but would not eliminate the possible time lag due to BG-to-IG glucose transport and the sensor processing time (instrument delay). Because such a time lag could greatly influence the accuracy of CGM, a number of studies were dedicated to its investigation, yielding various results [31,32,33,34]. For example, it was hypothesized that if glucose fall is due to peripheral glucose consumption the physiologic time lag would be negative, i.e. fall in IG would precede fall in BG [28,35]. In most studies IG lagged behind BG (most of the time) by 4-10 minutes, regardless of the direction of BG change [30,31]. The formulation of the push-pull phenomenon offered reconciliation of these results and provided arguments for a more complex BG-IG relationship than a simple constant or directional time lag [34,36]. In addition, errors from calibration, loss of sensitivity, and random noise confound CGM data [37]. Nevertheless, the accuracy of CGM is increasing and may be reaching a physiological limit for subcutaneous glucose monitoring [38,39,40].

The Artificial Pancreas

The next step in the progression of diabetes management is automated glucose control, or the artificial pancreas, which links a continuous glucose monitor with an insulin pump. A key element of this combination is a closed-loop control algorithm or method, which monitors blood glucose fluctuations and the actions of the insulin pump, and recommends insulin delivery at appropriate times.

The artificial pancreas idea can be traced back to developments that took place over thirty years ago when the possibility for external BG regulation in people with diabetes had been established by studies using intravenous (i.v.) glucose measurement and i.v. infusion of glucose and insulin. Systems such as the Biostator™ have been introduced and used in hospital settings to maintain normoglycemia (or euglycemia) by exerting both positive (via glucose or glucagon) and negative (via insulin) control [51,52,53,54,55]. Detailed descriptions of the major early designs can be found in [56,57,58,59,60,61]. More work followed, spanning a broader range of BG control techniques, powered by physiologic mathematical modeling and computer simulation control [62,63,64,65]. A review of methods for i.v. glucose control can be found in [66]. However, i.v. closed-loop control remains cumbersome and unsuited for outpatient use. An alternative to extracorporeal i.v. control has been presented by implantable intra-peritoneal (i.p.) systems employing intravenous BG sampling and i.p. insulin delivery [67,68]. The implementation of these systems, however, requires considerable surgery. Thus, with the advent of minimally-invasive subcutaneous (s.c.) CGM, increasing academic and industrial effort has been focused on the development of s.c.-s.c. systems, using CGM coupled with an insulin infusion pump and a control algorithm or method [69,70,71,72]. In September 2006, the Juvenile Diabetes Research Foundation (JDRF) initiated the Artificial Pancreas Project and funded a consortium of centers to carry closed-loop control research [73]. So far, encouraging pilot results have been reported by several centers [74,75,76,77,78].

Thus, in the past 30 years the monitoring and control of BG levels in diabetes has progressed from assessment of average glycemia once in several months, through daily SMBG, to minutely CGM. The increasing temporal resolution of the monitoring technology has enabled increasingly intensive diabetes treatment, from daily insulin injections or oral medication, through insulin pump therapy, to the artificial pancreas of the near future.

BRIEF SUMMARY OF THE INVENTION

As evident from the discussion above, a multitude of methods exist for BG monitoring and control in diabetes, ranging from traditional SMBG, medication, and MDI treatment, to CGM and artificial pancreas. These methods are currently dissimilar and there is no system that can handle more than one monitoring or control method at a time. An aspect of an embodiment of the present invention introduces the first flexible system capable of utilizing data from different monitoring techniques and capable of providing assistance to patients with diabetes at several scalable levels, ranging from advice about long-term trends and prognosis to real-time automated closed-loop control (artificial pancreas). These scalable monitoring and treatment strategies are delivered by a unified system—named by the present inventors as the Diabetes Assistant (DiAs) platform—that provides a foundation for implementation of various monitoring, advisory, and automated diabetes treatment algorithms or methods. The DiAs recommendations are tailored to the specifics of an individual patient, and to the patient risk assessment at any given moment. Some non-limiting and exemplary unique characteristics of DiAs are:

Informed by a Body Sensor Network;
Modular—layered architecture distributes data processing tasks across various application modules; individual modules are easily replaceable;
Scalable—naturally support new and expanded functionality, multiple data sources, and multiple data utilization strategies;
Portable—DiAs can run easily on portable computing devices, such as a cell phone, tablet computer, portal digital assistant (PDA), etc; thus it is deployable on a wide variety of rugged, inexpensive, and readily available devices;
Local and Global modes of operation—certain processes and patient interactions are available through the portable device; other services and remote monitoring of subject and system states are available via wireless communications (e.g. 30, WiFi, etc.).

According to one aspect of the invention, a system is provided for managing glycemic control of a patient, comprising an input module configured to accept input data from one or more of a plurality of diverse blood glucose measurement devices and one or mom of a plurality of diverse insulin delivery devices; a data classifier module configured to classify data accepted by said input module and to determine appropriate processing of said input data according to its classification; a patient state estimation module configured to process input data in accordance with at least one data processing algorithm corresponding to the classification of the input data as determined by the data classifier module; a patient risk status module configured to determine a level of risk of said patient with respect to abnormal glycemic states using processed data from said patient state estimation module; and an output module configured to output advisory messages, patient alerts, and control signals for said blood glucose measurement devices and said insulin delivery devices based on the level of risk determined by said patient risk status module.

According to another aspect of the invention, a non-transitory computer-readable storage medium is provided containing computer-executable instructions for performing functions to carry out the system.

DETAILED DESCRIPTION OF THE INVENTION

Overview

Figure 5:
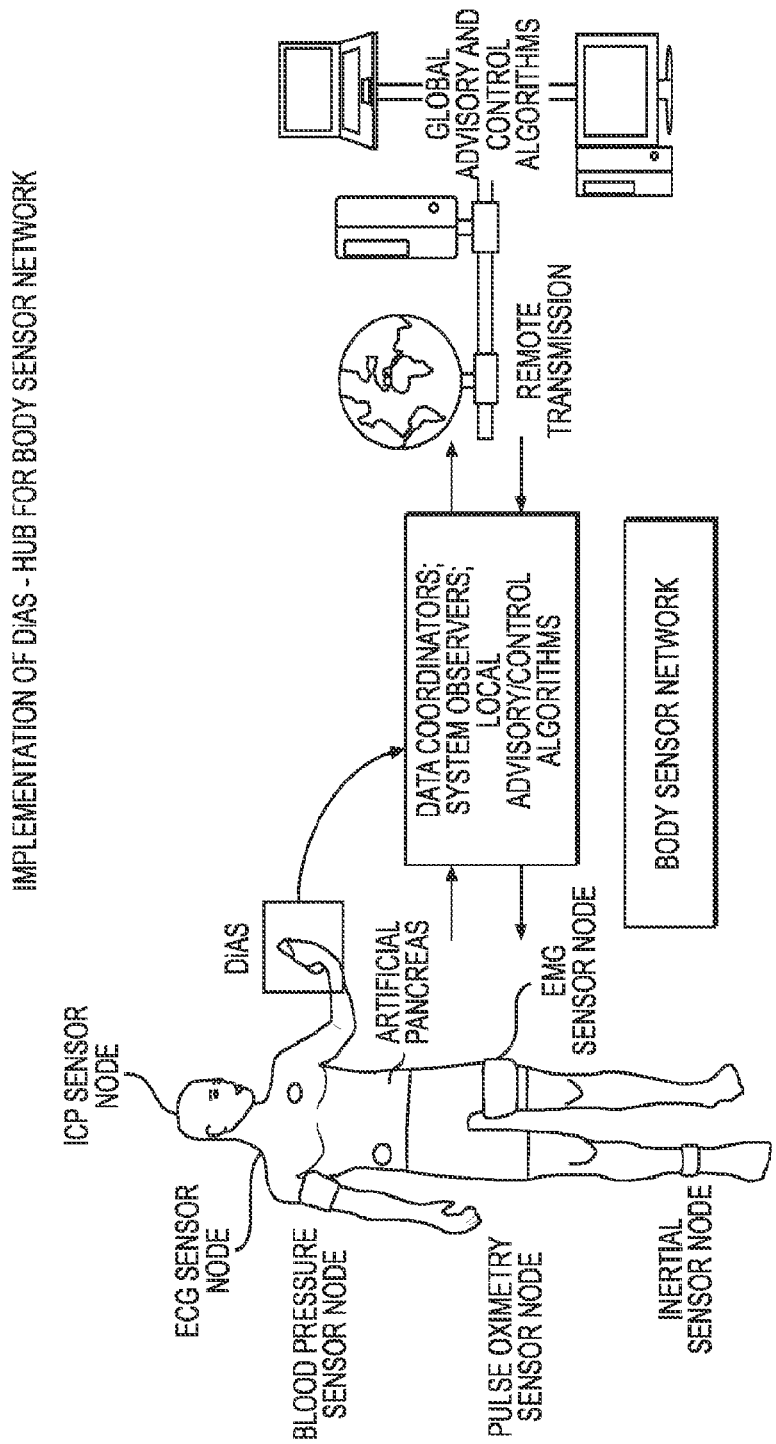
FIG. 5 is a schematic illustration of an implementation of the DiAs system as a hub for a body sensor network.

As shown in FIG. 5, a principal application of the DiAs system is the dynamic aggregation of body sensor network (BSN) data toward the goal of supporting long-term and efficient treatment of diabetes. DiAs is based on a wearable or handheld Diabetes Assistant platform that collects and pre-processes data from each individual's BSN, and uploads summary statistics to a remote location. The interface/algorithmic/methodology framework of DiAs: (i) ensures plug and play functionality with different metabolic sensors, (ii) allows for a general framework for prioritization of sensor data, making it clear how scarce computational, memory, and communication resources will be allocated to various sensing modalities, (iii) manages access to multiple uplink channels of varying reliability to a remote site, and (iv) resolves tradeoffs relating to where heavy computations should be performed (e.g., locally within the DiAs platform or remotely).

DiAs Inputs and Outputs

Figure 1:
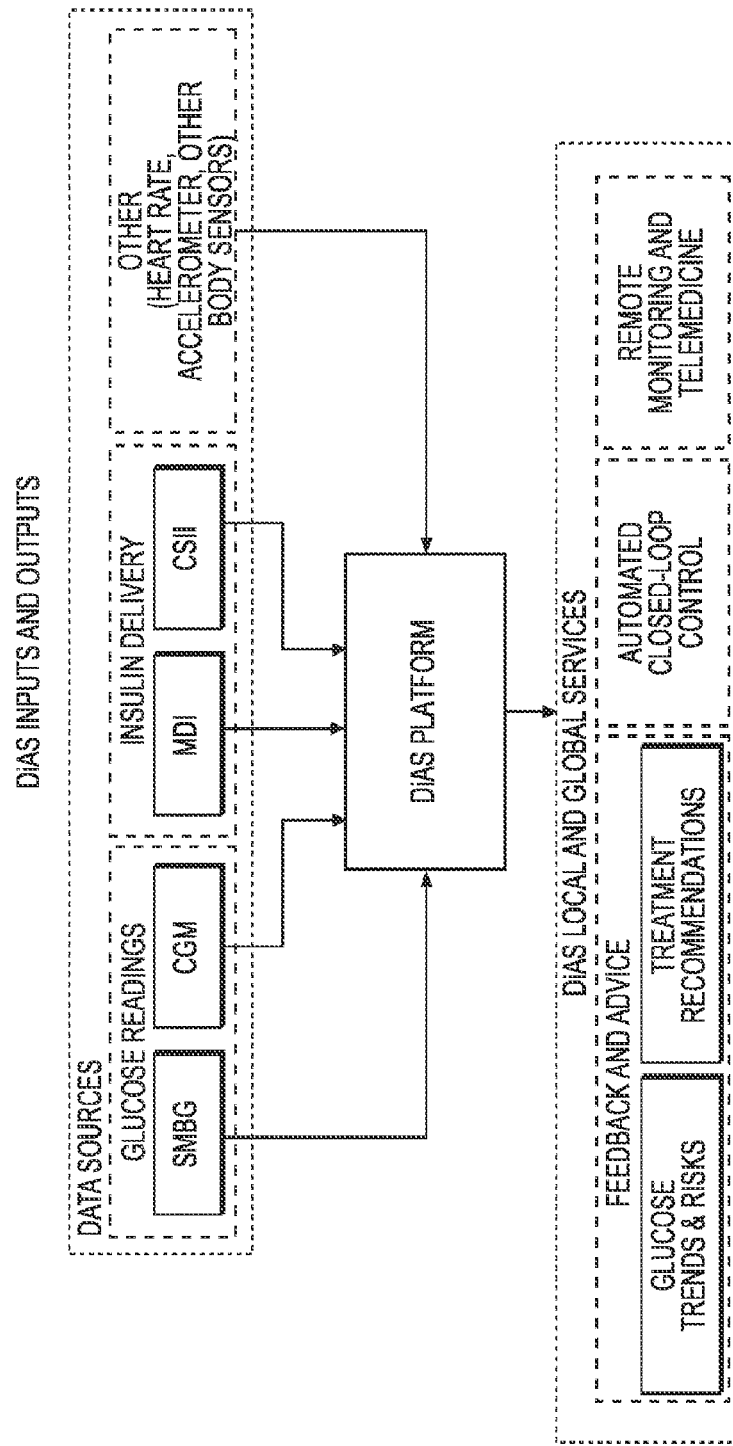
FIG. 1 is a schematic illustration of the DiAs platform inputs and outputs according to an aspect of the invention.

FIG. 1 presents the data sources available to the DiAs platform and the output services that DiAs provides. The data sources include SMBG, CGM, insulin delivery data (MDI and CSII), and other BSN data inputs such as heart rate, body accelerometer data, blood pressure, respiration, EKG data, etc. Depending on data availability (intermittent or continuous, blood glucose alone, or a multivariate data stream), DiAs provides different types of services that can be generally classified as:

Local Services: Applications that run on a portable device (e.g. a cell phone or tablet computer) communicating with an array of self-SMBG monitoring and CGM devices, an array of insulin delivery devices, and with other sensors in a BSN. The local service of DiAs is equipped with intelligent processing to provide an array of patient services, including safety supervision, local alerts, patient advisory functions, and closed-loop control (described further below);

Global Services: A centralized server communicating with multiple local services to provide different levels of data processing, advice, and training to patients; enable remote monitoring of glucose control profiles (e.g. parents monitoring remotely their children with diabetes); enable global alerts (e.g. a 911 call with GPS service to pinpoint a patient in need of emergency assistance), and to provide a physician-oriented information service presenting key data for multiple patients at a glance.

DiAs Processes

Figure 2:
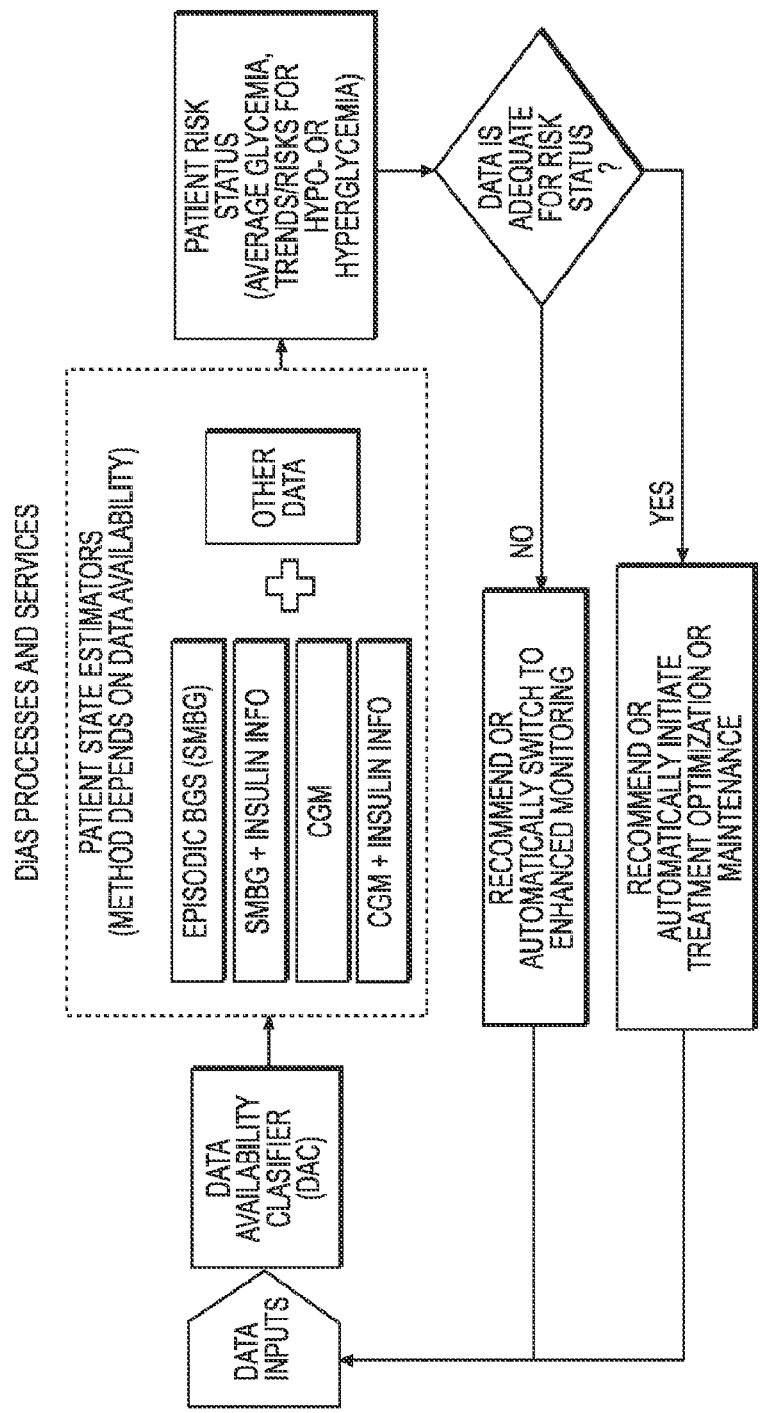
FIG. 2 is a schematic illustration of DiAs processes and services according to an aspect of the invention.

The general flow of DiAs processes is presented in FIG. 2 and includes the following steps:

1. Incoming data are directed to a Data Availability Classifier (DAC), which assesses the frequency, dimensionality, and quality of the incoming data. Based on the assessment, the DAC recommends different classes of data processing algorithms for the incoming data. Many of these algorithms already exist and are generally known, and can be classified as follows:

SMBG: This is currently the most established algorithmic class, including methods for the retrieval of SMBG data, evaluation of glycemic control, estimation of the risk for hypoglycemia, and information displays. SMBG acquisition and processing methods are described in several U.S. patents and published patent applications (=references [79-85] incorporated herein by reference). A 5-year clinical trial testing a SMBG-based system in 120 people with T1DM was recently completed, resulting in improved glycemic control, reduction of the risk for severe hypoglycemia, and high patient approval rating (results published in [86]);

CGM: Key elements applicable to these methods have been defined (references [87-92]). These methods are currently under development and testing in a large NIH-funded research project (Grant ROI DK 085623, Principal Investigator Dr. Boris Kovatchev);

CGM+insulin pump: Most of the methods applicable to COM alone have extensions capable of dealing with input/output to/from an insulin pump. We have recently completed an extensive series of clinical trials of closed-loop control to date.

Other: Heart rate changes can be used to indicate periods of physical activity, and more specifically periods of increased insulin sensitivity associated with exercise. These data inform diabetes control at several levels, including risk assessment for hypoglycemia and closed-loop control [93,94].

2. The first step of data processing is Patient State Estimation, given available data and using one of the methods described above. The state estimation results in assessment of the patient's risk status, which can be based on the risk analysis metrics presented in the background discussion above, and on biosystem observers or sensors, which process physiologic (and possibly behavioral) data to produce quantitative biosystem state estimators. These algorithms or methods are based on underlying mathematical models of the human metabolism and a Kalman filter, which produces system state estimation. Each system state estimator is a physiological or behavioral parameter of importance to the functioning of a person. The ensemble (vector) of biosystem estimators for a particular person represents the status of this person in terms of the blood glucose trend, availability of insulin, and risk for hypoglycemia. In essence, biosystem observers personalize the metabolic observation to a specific subject and extract composite information from the vast array of raw data that allows the precise evaluation of the subject's condition. It is anticipated that the biosystem observers will reside within a wearable DiAs system, while their summarized output will be sent to both the local predictive and control algorithms or methods and to remote observers as follows:

The primary output from the Patient State Estimation will be assessment of the patient's risk status for hypo- or hyperglycemia, based on the risk analysis and the LBGI/HBGI presented above. If the data quality and density is adequate for the risk status of the patient (e.g. the patient is in a steady state performing regular SMBG resulting in LBGI and HBGI lower than certain preset thresholds), then DiAs refers the data to algorithms that maintain the current patient status or fine-tune the patient's glycemic control. These algorithms can work in either an advisory or automated (closed-loop control) mode as follows:
  In advisory mode, DiAs activates the following services modules:
    Advisory Module 1: Prediction of elevated risk for hypoglycemia (24 hours ahead);
    Advisory Module 2: Bolus calculator suggesting pre-meal insulin doses;
    Advisory Module 3: Suggestion of basal rate profiles for the next 24 hours.
  In closed-loop control mode, DiAs activates the following service modules:
    Control Module 1: Real-time detection and prevention of hypoglycemia;
    Control Module 2: Stochastic control of pre-meal insulin boluses, and
    Control Module 3: Deterministic control of basal rate and overnight steady state.
If the data quality and density is inadequate for the risk status of the patient (e.g. the patient is at high risk for hypoglycemia, hyperglycemia, or both as indicated by the LBGI and HBGI exceeding certain preset thresholds), then:
  In advisory mode, DiAs recommends enhanced monitoring (e.g. more frequent SMBG or switching to CGM for a certain period of time);
  In automated control mode. DiAs switches the monitoring device to higher frequency SMBG measurement or to CGM mode (Note: such flexible monitoring devices are not currently manufactured, but are anticipated to be available in the future).

Figure 3:
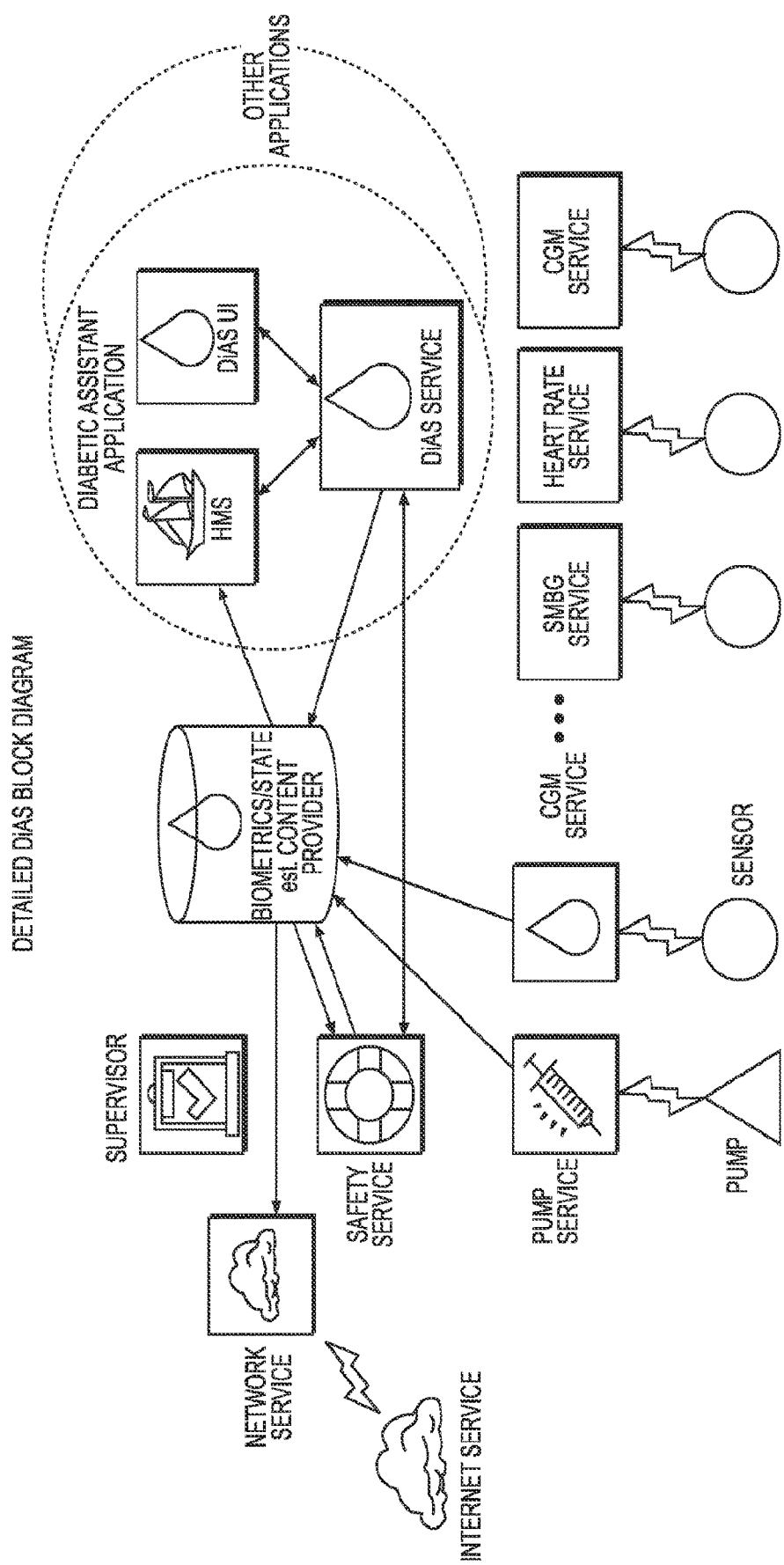
FIG. 3 is a block diagram of the DiAs system including applications and communication functions according to an embodiment of the invention.
Figure 4:
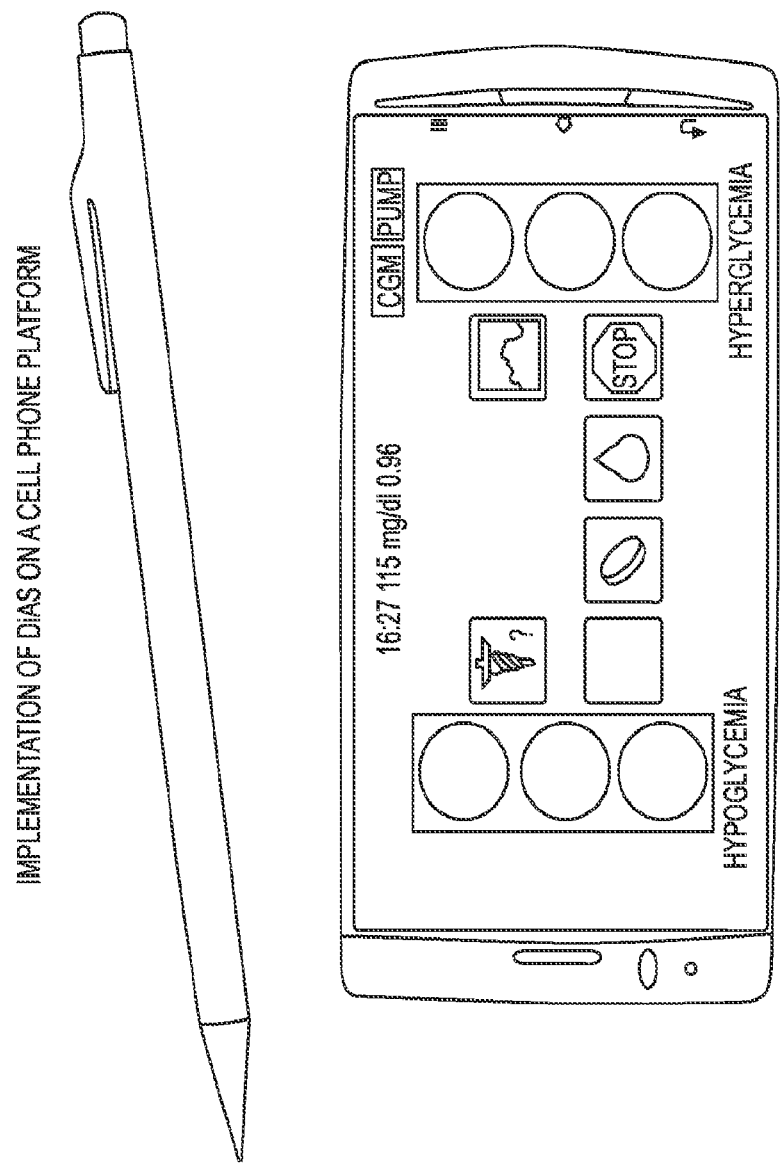
FIG. 4 shows an example implementation of the DiAs system on a cell phone platform according to an embodiment of the invention.

FIG. 3 presents a detailed schematic of the DiAs architecture:
  Central to this architecture is the Biometric State Estimator, which is the hub for exchange of data between the DiAs monitoring devices and algorithmic services or related methods. The Biometric State Estimator may also exchange data with remote physicians and/or patient care centers over the Internet through a network interface;
  The inputs used for state estimation are provided by various peripheral devices that monitor blood glucose fluctuations (SMBG Service, CGM Service), execute insulin delivery (Pump Service), or monitor other physiological parameters (Heart Rate Service, Esc. Service) as shown in FIG. 3;
  In turn, the Biometric State Estimator provides feedback to these devices as determined by a Safety Service, which assesses the integrity of the received data and judges whether the peripheral input/output devices are functioning properly. Methods employed by the Safety Service include previously introduced detection of CGM sensor errors [91] or judging the safety of insulin delivery [92];
  DiAs Applications may include various advisory and/or control algorithms, system and patient state alarms and indicators. These applications may be external to the DiAs system, and may be developed by third parties. Such applications may use DiAs services provided that they comply with the data exchange standards of the system. For example, a Hyperglycemia Mitigation Service (HMS) is a closed-loop control algorithm or method included in one of the embodiments of DiAs;
  The user interface with the DiAs system can be custom designed to meet the needs of specific DiAs implementations. One such implementation of a user interface is shown in FIG. 4:
    Two "traffic lights" signify the patient's present risk status for hypoglycemia and hyperglycemia, respectively, indicating low risk (green light), moderate risk/system action to mitigate the risk (yellow light) and high risk/necessity for immediate human intervention (red light);
    Several system/patient status inquiry icons open additional interfaces allowing the patient to access graphical and numerical representation of his/her glucose control, or inform the system of events (such as carbohydrate intake or exercise), which are treated as additional inputs by the DiAs analytical system;
  Network service (described in the next section) ensures remote monitoring and transmission of alerts and critical information in high-risk states.

Implementation of DiAs

FIG. 5 shows two major components of a DiAs implementation as a Body Sensor Network:
  Local Services (within the wearable/portable DiAs device) use predictive and control algorithms or methods based on simplified models of the human metabolic system that are trackable in real time. These are simple, typically linearized macro-level models that focus only on the principal system components. One example of such a model is the classic Minimal Model of Glucose Kinetics developed 30 years ago [95]. Available algorithms or methods include assessment, prediction, and control of glucose fluctuations in diabetes:
    Risk analysis of metabolic state with respect to normative limits;
    Detection of abrupt system changes, i.e. transitions of the system (person) from a stable to a critical state;
    Prediction of trends and gradual system changes, and outcome evaluation;
    Estimation of the probability for abrupt critical transitions;
    Warnings, alarms, and advisory messages when critical thresholds are approached;
    Automated intervention to prevent critical events;
    Communication to remote location and global algorithms or methods.

As shown in FIG. 5, a portable DiAs device (such as shown in FIG. 4) is communicatively connected (e.g. wirelessly through a wireless communication protocol such as Bluetooth. IEEE 802.11, etc.) to a plurality of BSN sensors, such as an ICP sensor, ECG sensor, blood pressure sensor, pulse oximetry sensor, inertial sensor, EMG sensor, artificial pancreas sensor, etc. Additionally, the DiAs device may have an interface to accept SMBG data.

Global services rely on predictive and control algorithms or methods deployed at a central location and receiving information from an array of individual system observers. These algorithms or methods will be based on large-scale probability models, risk analysis, clustering, and discriminant algorithms or methods. The output of these algorithms or methods will allow:

The monitoring of vital signs and metabolic processes by health care providers;

The detection of critical cases that require immediate intervention;

Collection of population-level anonymous public health statistics of interest to health care organizations.

Software/Hardware Implementation: Central to DiAs is a scalable software stack with a modular design that can be efficiently adapted to a variety of hardware platforms. The software architecture, the availability of suitable hardware platforms and opportunities to transfer software modules to commercial partners will factor into the choice of DiAs operating systems. For clinical trials and ambulatory implementation, hardware is needed that is portable, rugged, reliable, inexpensive and easily available. In this regard, a cell phone or a tablet computer could be selected. Consequently, the DiAs system may run within a customized version of the Android operating system. Android has a robust development environment, is available with source code, is backed by Google and runs on an ever-increasing array of cell phones and tablets from a variety of manufacturers. Android is being adopted by many commercial developers for new embedded software projects. Although many current products with embedded control software either have no operating system at all or use a simple control loop the trend is towards basing new embedded software projects on Android and embedded Linux. Since Android is built on top of Linux, an Android-based operating system for DiAs would allow transfer of software code to industry partners for commercial use. Android also provides a rich software development kit that supports multi-touch graphical user interface design, data communications, geo-location and telephony. Specifically:

At the highest level the AAPP Software Stack is composed of three major functional blocks: Device I/O Services, Core Services, and Control. As described above, FIG. 3 presents a diagram of the software stack depicting these blocks.

Device I/O Services handles all communication with sensors, pumps and other devices and provides a data interface to other elements of the system. The Device I/O modules store SMBG, CGM, and delivered insulin data and provide it to other components upon request.

Device I/O modules also implement a sensor and pump command service that validates and delivers commands received from the Safety Service.

Core Services is responsible for providing a runtime environment for applications such as the Closed-Loop Control App or the User Advice App and for supervising their operation. It generates state estimates based upon available data and provides this data to applications upon request.

Safety Service screens insulin bolus commands for safety before delivering them to the pump module and monitors the functioning of I/O devices detecting errors and potentially unsafe deviations.

While a preferred operating system has been discussed above, it will be recognized by those skilled in the art that the DiAs system may be implemented using any operating system that has features necessary to implement the DiAs system as contemplated above.

Figure 7:
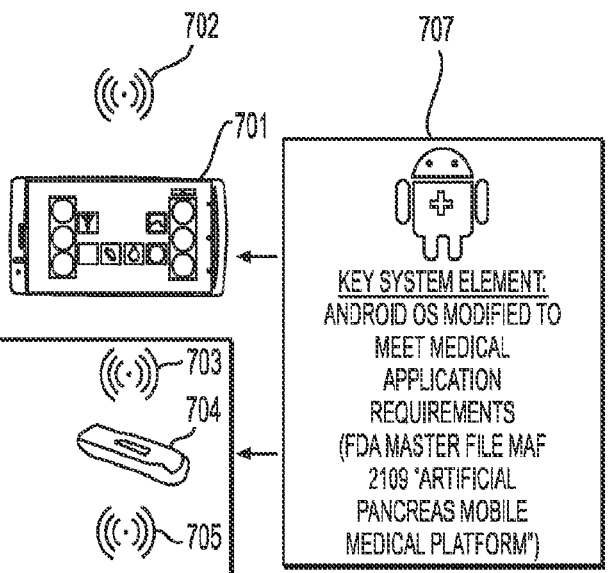
FIG. 7 is a schematic diagram showing another example implementation of the DiAs system on a central server over a network, enabling remote monitoring, safety assurance, telemedicine and database building to a further embodiment of the invention.
Figure 7:
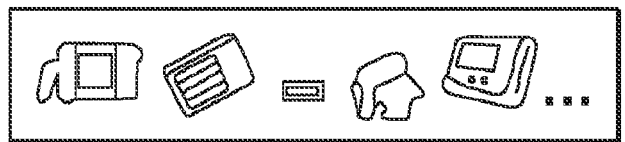
Figure 7:
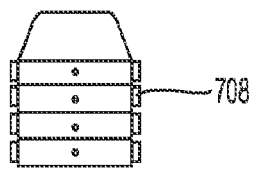

FIG. 7 shows a further example embodiment of a DiAs system in accordance with the invention. According to this embodiment, local patient functions including a user interface and control algorithms as disclosed above are performed on a smart-phone platform 701. Additionally, the smart-phone 701 connects to a central server or data exchange node 708 via a wireless connection 702 (e.g., a Wi-Fi, 3G or other similar wireless network connection). In a preferred embodiment, the connection 702 is a one-way connection from the smart-phone 701 to the central node or server, i.e. the central node or server does not transmit any substantive content to the smart-phone 701.

The smart-phone 701 sends patient data from the DiAs system user interface and control application(s) running on the smart-phone to the central node or server over the wireless network connection 702. The data from a plurality of smart-phones 701 each provided to an individual patient are collected by the central server 708 and used for safety assurance, monitoring, telemedicine and database building purposes.

The smart-phone 701 further has a communications connection 703 (either wired or wireless) to a DiAs hub device 704. Hub 704 is a meter-based platform that connects via one or more wireless connections 705 to a number of peripheral devices 706, for example, an insulin pump, a continuous glucose monitoring (CGM) device, etc. Hub 704 functions to ensure proper inter-device connection between the peripheral devices 706 and the smart-phone 701 running the DiAs local applications. Meter-based Hub 704 further functions to confirm SMBG readings from the peripheral devices 706.

In a preferred example embodiment, the smart-phone 701 and DiAs hub 704 run an operating system (OS) such as Android or other equivalent OS modified to meet medical application requirements, such as may be mandated by relevant authorities such as the FDA.

Figure 6:
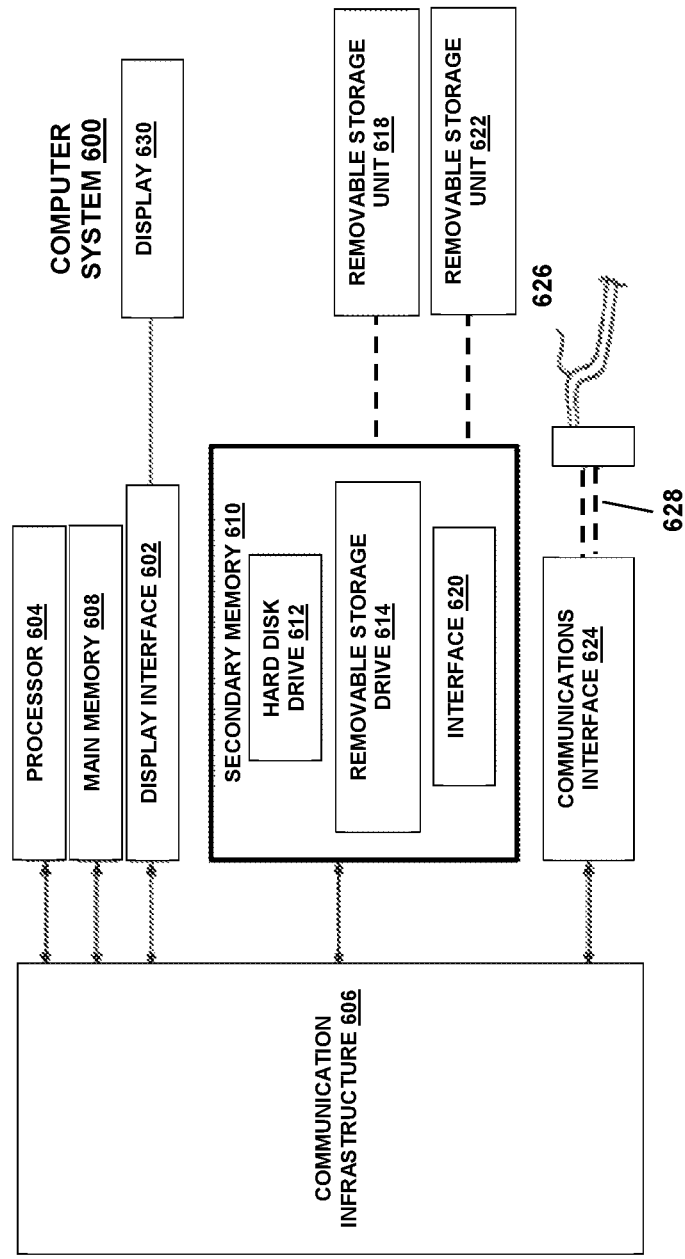
FIG. 6 is a schematic block diagram of an example data processing system for implementation of the present invention in whole or in part.

Turning now to FIG. 6, a functional block diagram is shown for a computer system 600 for exemplary implementation of an embodiment or portion of an embodiment of the present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 600 as illustrated in FIG. 6. The computer system 600 may includes one or more processors, such as processor 604. The Processor 604 is connected to a communication infrastructure 606 (e.g., a communications bus, cross-over bar, or network). The computer system 600 may include a display interface 602 that forwards graphics, text, and/or other data from the communication infrastructure 606 (or from a frame buffer not shown) for display on the display unit 630. Display unit 630 may be digital and/or analog.

The computer system 600 may also include a main memory 608, preferably random access memory (RAM), and may also include a secondary memory 610. The secondary memory 610 may include, for example, a hard disk drive 612 and/or a removable storage drive 614, representing a floppy disk drive, a magnetic tape drive, an optical disk drive, a flash memory, etc. The removable storage drive 614 reads from and/or writes to a removable storage unit 618 in a well known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other means for allowing computer programs or other instructions to be loaded into computer system 600. Such means may include, for example, a removable storage unit 622 and an interface 620. Examples of such removable storage units/interfaces include a program cartridge and cartridge interface (such as that found in video game devices), a removable memory chip (such as a ROM, PROM, EPROM or EEPROM) and associated socket, and other removable storage units 622 and interfaces 620 which allow software and data to be transferred from the removable storage unit 622 to computer system 600.

The computer system 600 may also include a communications interface 624. Communications interface 124 allows software and data to be transferred between computer system 600 and external devices. Examples of communications interface 624 may include a modem, a network interface (such as an Ethernet card), a communications port (e.g., serial or parallel, etc.), a PCMCIA slot and card, a modem, etc. Software and data transferred via communications interface 624 are in the form of signals 628 which may be electronic, electromagnetic, optical or other signals capable of being received by communications interface 624. Signals 628 are provided to communications interface 624 via a communications path (i.e., channel) 626. Channel 626 (or any other communication means or channel disclosed herein) carries signals 628 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 614, a hard disk installed in hard disk drive 612, and signals 628. These computer program products ("computer program medium" and "computer usable medium") are means for providing software to computer system 600. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 608 and/or secondary memory 610. Computer programs may also be received via communications interface 624. Such computer programs, when executed, enable computer system 600 to perform the features of the present invention as discussed herein. In particular, the computer programs, when executed, enable processor 604 to perform the functions of the present invention. Accordingly, such computer programs represent controllers of computer system 600.

In an embodiment where the invention is implemented using software, the software may be stored in a computer program product and loaded into computer system 600 using removable storage drive 614, hard drive 612 or communications interface 624. The control logic (software or computer program logic), when executed by the processor 604, causes the processor 604 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

REFERENCES

The following patents, applications and publications as listed below and throughout this document are hereby incorporated by reference in their entirety herein.

1. Reichard P, Phil M. Mortality and treatment side effects during long-term intensified conventional insulin treatment in the Stockholm Diabetes Intervention study. *Diabetes* 43: 313-317, 1994
2. The Diabetes Control and Complications Trial Research Group. The effect of intensive treatment of diabetes on the development and progression of long-term complications of insulin-dependent diabetes mellitus. *N Engl J Med* 329: 978-986, 1993
3. U K Prospective Diabetes Study Group (UKPDS). Intensive blood-glucose control with sulphonylureas or insulin compared with conventional treatment and risk of complications in patients with type 2 diabetes. *Lancet* 352: 837-853, 1998
4. Cryer P E. Hypoglycaemia: The limiting factor in the glycaemic management of type I and type II diabetes. *Diabetologia* 45: 937-948, 2002
5. Cryer P E: Hypoglycemia: The Limiting factor in the management of IDDM. *Diabetes* 43: 1378-1389, 1994
6. Clarke W L, Cox D, Gonder-Frederick L A, Carter W, Pohl S L. Evaluating the clinical accuracy of self-blood glucose monitoring systems. *Diabetes Care*, 10: 622-628, 1987.
7. The diabetes research in children network (DirecNet) study group. A multicenter study of the accuracy of the One Touch® Ultra® home glucose meter in children with Type 1 diabetes. *Diabetes Technol Ther*, 5: 933-942, 2003
8. Kovatchev B P, Cox D J, Gonder-Frederick L A Young-Hyman D, Schlundt D, Clarke W L. Assessment of risk for severe hypoglycemia among adults with IDDM: Validation of the Low Blood Glucose index, *Diabetes Care* 21: 1870-1875, 1998.

9. Cox D J, Kovatchev B. Julian D, Gonder-Frederick L A, Polonsky W H, Schlundt D G, Clarke W L. Frequency of severe hypoglycemia in IDDM can be predicted from self-monitoring blood glucose data. *J Clin Endocrinol Metab* 79: 1659-1662, 1994.

10. Kovatchev B P, Cox D J, Kumar A, Gonder-Frederick L A and W L Clarke. Algorithmic Evaluation of Metabolic Control and Risk of Severe Hypoglycemia in Type 1 and Type 2 Diabetes Using Self-Monitoring Blood Glucose (SMBG) Data. *Diabetes Technol Ther*, 5 (5): 817-828, 2003.

11. Cox D J, Gonder-Frederick L A, Ritterband L, Clarke W L, and Kovatchev B P. Prediction of Severe Hypoglycemia. *Diabetes Care*, 30: 1370-1373, 2007.

12. Kovatchev B P, Cox D J, Farhy L S, Straume M, Gonder-Frederick L A, Clarke, W L. Episodes of Severe Hypoglycemia in Type 1 Diabetes are Preceded, and Followed, within 48 Hours by Measurable Disturbances in Blood Glucose. *J Clin Endocrinol Metab*, 85: 4287-4292, 2000.

13. Kovatchev B P, Straume M, Cox D J, Farhy L S. Risk analysis of blood glucose data: A quantitative approach to optimizing the control of insulin dependent diabetes. *J of Theoretical Medicine*, 3:1-10, 2001.

14. Kovatchev B P, Cox D J, Gonder-Frederick L A and W L Clarke. Symmetrization of the blood glucose measurement scale and its applications. *Diabetes Care*, 20: 1655-1658, 1997.

15. Mastrototaro J. J. The MiniMed Continuous Glucose Monitoring System. *Diabetes Technol Ther*, 2: Supplement 1: S-13-S-18, 2000.

16. Bode B. W. Clinical Utility of the Continuous Glucose Monitoring System. *Diabetes Technol Ther*, 2: Supplement 1: S-35-S-42, 2000.

17. Feldman B, Brazg R, Schwartz S, Weinstein R. A continuous glucose sensor based on wired enzyme technology results from a 3-day trial in patients with Type 1 diabetes. *Diabetes Technol Ther*, 5: 769-778, 2003.

18. The diabetes research in children network (DirecNet) study group. The accuracy of the CGMS™ in children with Type 1 diabetes: Results of the diabetes research in children network (DirecNet) accuracy study. *Diabetes Technol Ther*, 5: 781-790, 2003.

19. Kovatchev B P, Anderson S M, Heinemann L, Clarke W L. Comparison of the numerical and clinical accuracy of four continuous glucose monitors. *Diabetes Care*, 31: 1160-1164, 2008.

20. Deiss, D, Bolinder, J, Riveline, J, Battelino, T, Bosi, E, Tubiana-Rufi, N, Kerr, D, Phillip, M: Improved glycemic control in poorly controlled patients with type 1 diabetes using real-time continuous glucose monitoring. *Diabetes Care* 29: 2730-2732, 2006.

21. Garg, K, Zisser, H, Schwartz, S, Bailey. T, Kaplan, R, Ellis, S, Jovanovic, L: Improvement in Glycemic Excursions With a Transcutaneous, Real-time Continuous Glucose Sensor. *Diabetes Care* 29:44-50, 2006.

22. Kovatchev B P, Clarke W L. Continuous glucose monitoring reduces risks for hypo- and hyperglycemia and glucose variability in diabetes. *Diabetes*, 56, Supplement 1: 0086OR, 2007.

23. The Juvenile Diabetes Research Foundation Continuous Glucose Monitoring Study Group: Continuous glucose monitoring and intensive treatment of type 1 diabetes. *N Engl J Med*, 359:1464-76, 2008.

24. Klonoff D C: Continuous glucose monitoring: roadmap for 21st century diabetes therapy. *Diabetes Care* 28:1231-1239, 2005.

25. Hovorka R: Continuous glucose monitoring and closed-loop systems. *Diabet Med* 23:1-12, 2006.

26. Klonoff D C: The Artificial Pancreas: How Sweet Engineering Will Solve Bitter Problems. *J Diabetes Sci Technol*, 1: 72-81, 2007.

27. Hirsch I B, Armstrong D, Bergenstal R M, Buckingham B, Childs B P, Clarke W L, Peters A, Wolpert H. Clinical Application of Emerging Sensor Technologies in Diabetes Management: Consensus Guidelines for Continuous Glucose Monitoring. *Diabetes Tech Ther*, 10: 232-246, 2008.

28. Rebrin K, Steil G M, van Antwerp W P, and Mastrototaro J J: Subcutaneous glucose predicts plasma glucose independent of insulin: implications for continuous monitoring. *Am J Physiol Endocrinol Metab*, 277:E561-E571, 1999.

29. Rebrin K and Steil G M: Can interstitial glucose assessment replace blood glucose measurements? *Diabetes Technol Ther*, 2:461-472, 2000.

30. Steil G M, Rebrin K. Hariri F, Jinagonda S, Tadros S, Darwin C, Saad M F: Interstitial fluid glucose dynamics during insulin-induced hypoglycaemia. *Diabetologia*, 48:1833-40, 2005.

31. Boyne M, Silver D, Kaplan J, and Saudek C: Timing of Changes in Interstitial and Venous Blood Glucose Measured With a Continuous Subcutaneous Glucose Sensor. *Diabetes*, 52:2790-2794, 2003.

32. Kulcu E, Tamada J A, Reach G. Potts R O, Lesho M J: Physiological differences between interstitial glucose and blood glucose measured in human subjects. *Diabetes Care*, 26:2405-2409, 2003.

33. Stout P J, Racchini J R, Hilgers M E: A Novel Approach to Mitigating the Physiological Lag between Blood and Interstitial Fluid Glucose Measurements. *Diabetes Technol Ther*, 6:635-644, 2004.

34. Wentholt I M E, Hart A A M, Hoekstra J B L, DeVries J H. Relationship Between Interstitial and Blood Glucose in Type 1 Diabetes Patients: Delay and the Push-Pull Phenomenon Revisited. *Diabetes Technol Ther*, 9:169-175, 2004.

35. Wientjes K J, Schoonen A J: Determination of time delay between blood and interstitial adipose tissue glucose concentration change by microdialysis in healthy volunteers. *Int J Artif Organs*, 24:884-889, 2001.

36. Aussedat B, Dupire-Angel M, Gifford R, Klein J C, Wilson G S, Reach G: Interstitial glucose concentration and glycemia: implications for continuous subcutaneous glucose monitoring. *Am J Physiol Endocrinol Metab*, 278:E716-E728, 2000.

37. Kovatchev B P and Clarke W L. Peculiarities of the Continuous Glucose Monitoring Data Stream and Their Impact on Developing Closed-Loop Control Technology. *J Diabetes Sci Technol*, 2:158-163, 2008.

38. Clarke W L, Kovatchev B P: Continuous glucose sensors—continuing questions about clinical accuracy. *J Diabetes Sci Technol* 1:164-170, 2007.

39. The Diabetes Research in Children Network (DirecNet) Study Group. The Accuracy of the Guardian R T Continuous Glucose Monitor in Children with Type 0.1 Diabetes. *Diabetes Tech Ther*, 10: 266-272, 2008.

40. Garg S K, Smith J, Beatson C, Lopez-Baca B, Voelmle M, Gottlieb P A. Comparison of Accuracy and Safety of the SEVEN and the Navigator Continuous Glucose Monitoring Systems. *Diabetes Tech Ther*, 11: 65-72, 2009.

41. T. Heise, T. Koschinsky, L. Heinemann, and V. Lodwig, "Glucose Monitoring Study Group. Hypoglycemia warning signal and glucose sensors: requirements and concepts," *Diabetes Technol Ther*, 5: 563-571, 2003.

42. B. Bode, K. Gross, N. Rikalo, S. Schwartz, T. Wahl, C. Page, T. Gross, and J. Mastrototaro. Alarms based on real-time sensor glucose values alert patients to hypo- and hyperglycemia: the guardian continuous monitoring system. *Diabetes Technol Ther,* 6: 105-113, 2004.

43. G. McGarraugh and R. Bergenstal, "Detection of hypoglycemia with continuous interstitial and traditional blood glucose monitoring using the FreeStyle Navigator Continuous Glucose Monitoring System," *Diabetes Technol Ther,* 11: 145-150, 2009.

44. S. E. Noujaim, D. Horwitz, M. Sharma, J. Marhoul. "Accuracy requirements for a hypoglycemia detector: an analytical model to evaluate the effects of bias, precision, and rate of glucose change," *J Diabetes Sci Technol.* 1: 653-668, 2007.

45. W. K. Ward, "The role of new technology in the early detection of hypoglycemia," *Diabetes Technol Ther,* 6: 115-117, 2004.

46. B. Buckingham, E. Cobry, P. Clinton, V. Gage, K. Caswell, E. Kunselman, F. Cameron, and H. P. Chase. Preventing hypoglycemia using predictive alarm algorithms and insulin pump suspension. *Diabetes Technol Ther,* 11: 93-97, 2009.

47. Miller M, Strange P: Use of Fourier Models for Analysis and Interpretation of Continuous Glucose Monitoring Glucose Profiles. *J Diabetes Sci Technol,* 1: 630-638, 2007.

48. Kovatchev B P, Gonder-Frederick L A, Cox D J, Clarke W L: Evaluating the accuracy of continuous glucose-monitoring sensors: continuous glucose-error grid analysis illustrated by TheraSense Freestyle Navigator data. *Diabetes Care,* 27:1922-28, 2004.

49. McDonnell C M, Donath S M, Vidmar S I, Werther G A, Cameron F J: A Novel Approach to Continuous Glucose Analysis Utilizing Glycemic Variation. *Diabetes Technol Ther,* 7: 253-263, 2005.

50. Clarke W L & Kovatchev B P. Statistical Tools to Analyze CGM Data. *Diabetes Technol Ther,* 11: S45-S54, 2009.

51. Albisser A M, Leibel B S, Ewart T G, Davidovac Z, Botz C K, Zinggg W. An artificial endocrine pancreas. *Diabetes,* 23:389-396, 1974.

52. Clemens A H, Chang P H, Myers R W. The development of Biostator, a glucose-controlled insulin infusion system. *Horm Metab Res Supplement,* 7: 23-33, 1977.

53. Marliss E B, Murray F T, Stokes E F, Zinman B, Nakhooda A F, Denoga A, Leibel B S, and Albisser A M: Normalization of glycemia in diabetics during meals with insulin and glucagon delivery by the artificial pancreas. *Diabetes* 26: 663-672, 1977.

54. Pfeiffer E F, Thum Ch, and Clemens A H: The artificial beta cell—A continuous control of blood sugar by external regulation of insulin infusion (glucose controlled insulin infusion system). *Horm Aetab Res* 487: 339-342, 1974.

55. Santiago J V, Clemens A H, Clarke W L Kipnis D M. Closed-loop and open-loop devices for blood glucose control in normal and diabetic subjects. *Diabetes,* 28: 71-84, 1979.

56. Broekhuyse H M. Nelson J D, Zinman B, and Albisser A M: Comparison of algorithms for the closed-loop control of blood glucose using the artificial beta cell. *IEEE Trans Biomed Eng* 28: 678-687, 1981.

57. Clemens A H: Feedback control dynamics for glucose controlled insulin infusion system. *MedProg Technol* 6: 91-98, 1979.

58. Cobelli C, Ruggeri A: Evaluation of portal/peripheral route and of algorithms for insulin delivery in the closed-loop control of glucose in diabetes. A modeling study. *IEEE Trans Biomed Eng* 30: 93-103, 1983.

59. E W, Campbell L V, Chia Y O, Meter H, and Lazarus L: Control of blood glucose in diabetics using an artificial pancreas. *Aust N Z J Med* 7: 280-286, 1977.

60. Fischer U, Jutzi E, Freyse E-J, and Salzsieder E: Derivation and experimental proof of a new algorithm for the artificial beta-cell based on the individual analysis of the physiological insulin-glucose relationship. *Endokrinologie* 71:65-75, 1978.

61. Salzsieder E, Albrecht G, Fischer U, and Fryse E-J: Kinetic modeling of the gluco-regulatory system to improve insulin therapy. *IEEE Trans Biomed Eng* 32: 846-855, 1985.

62. Brunetti P., Cobelli C., Cruciani P., Fabietti P. O., Filippucci F., Santeusanio F.: A simulation study on a self-tuning portable controller of blood glucose. *Int J Artificial Organs* 16:51-57, 1993.

63. Fischer U, Schenk W, Salzsieder E, Albrecht G, Abel P, and Freyse E-J: Does physiological blood glucose control require an adaptive strategy? *IEEE Trans Biomed Eng* 34:575-582, 1987.

64. Sorensen J T: A Physiologic Model of Glucose Metabolism in Man and its Use to Design and Assess Improved Insulin Therapies for Diabetes, Ph.D. dissertation, Dept Chemical Engineering, M I T, 1985.

65. Parker R S, Doyle F J 3rd, Peppas N A. A model-based algorithm for blood glucose control in Type I diabetic patients. *IEEE Trans Biomed Eng,* 48:148-157, 1999.

66. Parker R S, Doyle F J 3rd, Peppas N A. The intravenous route to blood glucose control. *IEEE Eng Med Biol,* 20:65-73, 2001.

67. Leblanc H, Chauvet D, Lombrail P Robert J J: Glycemic control with closed-loop intraperitoneal insulin in type I diabetes. *Diabetes Care,* 9:124-128, 1986.

68. Renard E: Implantable closed-loop glucose-sensing and insulin delivery: the future for insulin pump therapy, *Current Opinion in Pharmacology,* 2: 708-716, 2002.

69. Bellazzi R, Nucci G, Cobelli C: The subcutaneous route to insulin-dependent diabetes therapy: closed-loop and partially closed-loop control strategies for insulin delivery and measuring glucose concentration. *IEEE Eng Med Biol,* 20: 54-64, 2001.

70. Hovorka R. Chassin L J, Wilinska M E, et al. Closing the loop: the ADICOL experience. *Diabetes Technol Ther.* 6: 307-318, 2004.

71. Steil G M, Rebrin K, Darwin C, Hariri F, Saad M F. Feasibility of automating insulin delivery for the treatment of type 1 diabetes. *Diabetes,* 55: 3344-3350, 2006.

72. Clarke W L and Kovatchev B P. The Artificial Pancreas: How Close We Are to Closing the Loop? *Ped Endocrinol Rev,* 4: 314-316, 2007.

73. The JDRF e-Newsletter: Emerging Technologies in Diabetes Research, September, 2006.

74. Weinzimer S A, Steil G M, Swan K L, Dziura J, Kurtz N, Tamborlane W V: Fully automated closed-loop insulin delivery versus semi-automated hybrid control in pediatric patients with type 1 diabetes using an artificial pancreas. *Diabetes Care,* 31:934-939, 2008.

75. Clarke W L, Anderson S M, Breton M D, Patek S D, Kashmer L, and Kovatchev B P. Closed-Loop Artificial Pancreas Using Subcutaneous Glucose Sensing and insulin Delivery and a Model Predictive Control Algorithm: The Virginia Experience. *J Diabetes Sci Technol,* 3: 1031-1038, 2009.

76. Bruttomesso D, Farret A, Costa S, Marescotti M C, Vettore M, Avogaro A, Tiengo A, C. et al: Closed-Loop Artificial Pancreas Using Subcutaneous Glucose Sensing & Insulin Delivery, and a Model Predictive Control Algorithm: Preliminary Studies in Padova and Montpellier. *J Diabetes Sci Technol*, 3: 1014-1021, 2009.

77. Hovorka R, Allen J M, Elleri D, et al., Manual closed-loop insulin delivery in children and adolescents with type 1 diabetes: a phase 2 randomised crossover trial. *The Lancet*, 375: 743-751, 2010.

78. El-Khatib F H, Russell S J, Nathan D M, Sutherlin R G, Damiano E R. A Bihormonal Closed-Loop Artificial Pancreas for Type 1 Diabetes. *Science Transl Med*, 2: 27ra27, 2010.

79. Kovatchev B P & Cox D J. Method, system, and computer program product for the evaluation of glycemic control in diabetes from self-monitoring data; U.S. Pat. No. 7,025,425 issued on Apr. 11, 2006.

80. Kovatchev B P & Cox D J. Method, system, and computer program product for the evaluation of glycemic control in diabetes from self-monitoring data; U.S. Pat. No. 7,874,985 B2 issued on Jan. 25, 2011.

81. Kovatchev B P. Method, system, and computer program product for evaluation of blood glucose variability in diabetes from self-monitoring data; PCT/US2007/000370; 2007.

82. Kovatchev B P. Systems, methods and computer program codes for recognition of patterns of hyperglycemia and hypoglycemia, increased glucose variability, and ineffective self-monitoring in diabetes. PCT/US2008/0154513 A1, 2008.

83. Kovatchev B P and Breton M D. Method, System, and Computer Program Product for Visual and Quantitative Tracking of Blood Glucose Variability in Diabetes from Self-Monitoring Data. U.S. Provisional PCT/US2009/065725, 2009.

84. International Patent Application Serial No. PCT/US2010/047711, Kovatchev, et al., "Tracking the Probability for Imminent Hypoglycemia in Diabetes from Self-Monitoring Blood Glucose (SMBG) Data", filed Sep. 2, 2010.

85. Kovatchev B P and Breton M D. Method, system and computer program product for evaluation of insulin sensitivity, insulin/carbohydrate ratio, and insulin correction factors in diabetes from self-monitoring data; PCT/US2008/069416 and U.S. Publication Application US2010/0198520.

86. Kovatchev B P, Mendosa P, Anderson S M, Hawley J S, Ritterband L M, & Gonder-Frederick L. Effect of automated bio-behavioral feedback on the control of type 1 diabetes. *Diabetes Care*, 34:302-307, 2011

87. Kovatchev B P, Gonder-Frederick L A, Cox D J, Clarke W L. Method, system and computer program for evaluating the accuracy of blood glucose monitoring sensors/devices, U.S. Pat. No. 7,815,569 issued on Oct. 19, 2010.

88. Breton M D and Kovatchev B P. Method, system and computer program product for real-time detection of sensitivity decline in analyte sensors; PCT/US2007/082744, 2007.

89. Patek S D and Breton M D. LQG Artificial Pancreas Control System And Related Method. International Application Serial No. PCT/US2008/067723.

90. Kovatchev B P, Breton M D, and Patek S D. Method, System and Computer Program Product for CGM-Based Prevention of Hypoglycemia Risk Assessment and Smooth Reduction of Insulin. International Application Serial No. PCT/US2010/025405.

91. A. International Patent Application Serial No. PCT/US2011/029793, Kovatchev et al., entitled Method, System, and Computer Program Product for Improving the Accuracy of Glucose Sensors Using Insulin Delivery Observation in Diabetes," filed Mar. 24, 2011.

92. PCT/US2011/028163, Breton, et al., entitled "Method and System for the Safety, Analysis and Supervision of Insulin Pump Action and Other Modes of Insulin Delivery in Diabetes", filed Mar. 11, 2011.

93. Kovatchev B P and Breton M D. Method, system, and computer program product for the detection of physical activity by changes in heart rate, assessment of fast changing metabolic states, and applications to closed and open control loop in diabetes. PCT/US2007/085588; 2007.

94. Kovatchev B P, Patek S D, Breton M D. and. System Coordinator and Modular Architecture for Open-Loop and Closed-Loop Control for Diabetes. PCT/US2010/036629, filed May 28, 2010.

95. Bergman R N, Ider Y Z, Bowden C R, Cobelli C. Quantitative estimation of insulin sensitivity. *Am J Physiol*. 236:E667-E677, 1979.

The devices, systems, computer program products, and methods of various embodiments of the invention disclosed herein may utilize aspects disclosed in the following references, applications, publications and patents and which are hereby incorporated by reference herein in their entirety:

A. International Patent Application Serial No. PCT/US2011/029793, Kovatchev et al., entitled Method, System, and Computer Program Product for Improving the Accuracy of Glucose Sensors Using Insulin Delivery Observation in Diabetes," filed Mar. 24, 2011

B. PCT/US2011/028163, Breton, et al., entitled "Method and System for the Safety, Analysis and Supervision of Insulin Pump Action and Other Modes of Insulin Delivery in Diabetes", filed Mar. 11, 2011.

C. International Patent Application Serial No. PCT/US2010/047711, Kovatchev, et al., "Tracking the Probability for Imminent Hypoglycemia in Diabetes from Self-Monitoring Blood Glucose (SMBG) Data", filed Sep. 2, 2010.

D. International Patent Application Serial No. PCT/US2010/047386, Kovatchev, et al., "System, Method and Computer Program Product for Adjustment of Insulin Delivery (AID) in Diabetes Using Nominal Open-Loop Profiles", filed Aug. 31, 2010.

E. International Patent Application Serial No. PCT/US2010/040097, Kovatchev, et al., "System, Method, and Computer Simulation Environment for In Silico Trials in Prediabetes and Type 2 Diabetes", filed Jun. 25, 2010.

F. International Patent Application Serial No. PCT/US2010/036629, Kovatchev, et al., "System Coordinator and Modular Architecture for Open-Loop and Closed-Loop Control of Diabetes", filed May 28, 2010 (Publication No. WO 2010/138848, Dec. 2, 2010).

G. International Patent Application Serial No. PCT/US2010/025405, Kovatchev, et al., entitled "Method. System and Computer Program Product for CGM-Based Prevention of Hypoglycemia via Hypoglycemia Risk Assessment and Smooth Reduction Insulin Delivery," filed Feb. 25, 2010.

H. International Patent Application Serial No. PCT/US2009/065725. Kovatchev, et al., filed Nov. 24, 2009, entitled "Method, System, and Computer Program Product for Tracking of Blood Glucose Variability in Diabetes from Data."

I. International Patent Application Serial No. PCT/US2008/082063, Magni, et al., entitled "Model Predictive Control Based Method for Closed-Loop Control of Insulin Delivery in Diabetes Using Continuous Glucose Sensing", filed Oct. 31, 2008; U.S. patent application Ser. No. 12/740,275, Magni, et al., entitled "Predictive Control Based System and Method for Control of Insulin Delivery in Diabetes Using Glucose Sensing", filed Apr. 28, 2010.

J. International Patent Application Serial No. PCT/US2008/069416, Breton, et al., entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008, (Publication No. WO 2009/009528, Jan. 15, 2009); U.S. patent application Ser. No. 12/665,149, Breton, et al., "Method, System and Computer Program Product for Evaluation of Insulin Sensitivity, Insulin/Carbohydrate Ratio, and Insulin Correction Factors in Diabetes from Self-Monitoring Data", filed Dec. 17, 2009.

K. International Patent Application Serial No. PCT/US2008/067725, Kovatchev, et al., entitled "Method, System and Computer Simulation Environment for Testing of Monitoring and Control Strategies in Diabetes," filed Jun. 20, 2008, (Publication No. WO 2008/157781, Dec. 24, 2008); U.S. patent application Publication Ser. No. 12/664,444, Kovatchev, et al., filed Dec. 14, 2009, entitled "Method, System and Computer Simulation Environment for Testing of Monitoring and Control Strategies in Diabetes", (Publication No. 2010/0-179768, Jul. 15, 2010).

L. International Patent Application Serial No. PCT/US2008/067723, Patek, et al., entitled "LQG Artificial Pancreas Control System and Related Method", filed on Jun. 20, 2008.

M. U.S. patent application Ser. No. 12/516,044, Kovatchev, et al., filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes".

N. International Patent Application Serial No. PCT/US2007/085588, Kovatchev, et al., filed Nov. 27, 2007, entitled "Method, System. and Computer Program Product for the Detection of Physical Activity by Changes in Heart Rate, Assessment of Fast Changing Metabolic States, and Applications of Closed and Open Control Loop in Diabetes", (Publication No. WO2008/067284, Jun. 5, 2008)

O. U.S. patent application Ser. No. 11/943,226, Kovatchev, et al., filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes".

P. U.S. patent application Ser. No. 11/578,831, Kovatchev, et al., filed Oct. 18, 2006 entitled "Method, System and Computer Program Product for Evaluating the Accuracy of Blood Glucose Monitoring Sensors/Devices", (Publication No. US2007/0232878, Oct. 4, 2007), U.S. Pat. No. 7,815,569, Kovatchev, et al., issued Oct. 29, 2010

Q. International Application Serial No. PCT/US2005/013792, Kovatchev, et al., filed Apr. 21, 2005, entitled "Method, System, and Computer Program Product for Evaluation of the Accuracy of Blood Glucose Monitoring Sensors/Devices", (Publication No. WO 05106017, Nov. 10, 2005

R. International Patent Application Serial No. PCT/US01/09884, Kovatchev, et al., filed Mar. 29, 2001, entitled "Method, System, and Computer Program Product for Evaluation of Glycemic Control in Diabetes Self-Monitoring Data", (Publication No. WO 01/72208, Oct. 4, 2001).

S. U.S. patent application Ser. No. 10/240,228, Kovatchev, et al., filed Sep. 26, 2002, (Publication No. 0212317, Nov. 13, 2003), U.S. Pat. No. 7,025,425 B2, Kovatchev, et al., issued Apr. 11, 2006, entitled "Method, System, and Computer Program Product for the Evaluation of Glycemic Control in Diabetes from Self-Monitoring Data".

T. U.S. patent application Ser. No. 11/305,946, Kovatchev, et al., filed Dec. 19, 2005 entitled "Method, System, and Computer Program Product for the Evaluation of Glycemic Control in Diabetes from Self-Monitoring Data" (Publication No. 2006/0094947, May 4, 2006), U.S. Pat. No. 7,874,985, Kovatchev, et al., issued Jan. 25, 2011.

U. U.S. patent application Ser. No. 12/975,580, Kovatchev, et al., "Method, System, and Computer Program Product for the Evaluation of Glycemic Control in Diabetes from Self-Monitoring Data", filed Dec. 22, 2010.

V. International Patent Application Serial No. PCT/US2003/025053, Kovatchev, et al., filed Aug. 8, 2003, entitled "Method, System, and Computer Program Product for the Processing of Self-Monitoring Blood Glucose (SMBG) Data to Enhance Diabetic Self-Management", (Publication No. WO 2004/015539, Feb. 19, 2004).

W. U.S. patent application Ser. No. 10/524,094, Kovatchev, et al., filed Feb. 9, 2005 entitled "Managing and Processing Self-Monitoring Blood Glucose" (Publication No. 2005/214892, Sep. 29, 2005).

X. U.S. patent application Ser. No. 12/065,257, Kovatchev, et al., filed Aug. 29, 2008, entitled "Accuracy of Continuous Glucose Sensors", (Publication No. 2008/0314395, Dec. 25, 2008).

Y. International Patent Application Serial No PCT/US2006/033724, Kovatchev, et al., filed Aug. 29, 2006, entitled "Method for Improvising Accuracy of Continuous Glucose Sensors and a Continuous Glucose Sensor Using the Same", (Publication No. WO 07027691, Mar. 8, 2007).

Z. U.S. patent application Ser. No. 12/159,891, Kovatchev, B., filed Jul. 2, 2008, entitled "Method, System and Computer Program Product for Evaluation of Blood Glucose Variability in Diabetes from Self-Monitoring Data", (Publication No. 2009/0171589, Jul. 2, 2009).

AA. International Application No. PCT/US2007/000370, Kovatchev, B., filed Jan. 5, 2007, entitled "Method. System and Computer Program Product for Evaluation of Blood Glucose Variability in Diabetes from Self-Monitoring Data", (Publication No. WO 07081853, Jul. 19, 2007).

BB. U.S. patent application Ser. No. 11/925,689 and PCT International Patent Application No. PCT/US2007/082744, Breton, et al., both filed Oct. 26, 2007, entitled "For Method, System and Computer Program Product for Real-Time Detection of Sensitivity Decline in Analyte Sensors", (Publication Nos. 2008/0172205, Jul. 17, 2008 and WO 2008/052199, May 2, 2008).

CC. U.S. patent application Ser. No. 10/069,674, Kovatchev, et al., filed Feb. 22, 2002, entitled "Method and Apparatus for Predicting the Risk of Hypoglycemia".

DD. International Application No. PCT/US00/22886, Kovatchev, et al., filed Aug. 21, 2000, entitled "Method and Apparatus for Predicting the Risk of Hypoglycemia", (Publication No. WO 01/13786, Mar. 1, 2001).

EE. U.S. Pat. No. 6,923,763 B1, Kovatchev, et al., issued Aug. 2, 2005, entitled "Method and Apparatus for Predicting the Risk of Hypoglycemia".

FF. U.S. Patent Application Publication No. US 2004/0254434 A1, "Glucose Measuring Module and "Insulin Pump Combination", published Dec. 16, 2004, Goodnow, et al. Ser. No. 10/458,914, filed Jun. 10, 2003.

GG. U.S. Patent Application Publication No. US 2009/00697456 A1, Estes, et al., "Operating an infusion Pump System", published Mar. 12, 2009. Ser. No. 11/851,194, Sep. 6, 2007.
HH. Fernandez-Luque, et al., eDiab: A System for Monitoring. Assisting and Educating People with Diabetes", ICCHP 2006, LNCS 4061, pp. 1342-1349, 2006.
II. U.S. Pat. No. 6,602,191 B2, Quy, R., Method and Apparatus for Health and Disease Management Combining Patient Data Monitoring with Wireless Internet Connectivity, Aug. 5, 2003.
JJ. International Patent Application Publication No. WO 2008/064053 A2, Patel, et al., Systems and Methods for Diabetes Management Using Consumer Electronic Devices, May 29, 2008; International Patent Application Serial No. PC/US2007/084769, filed Nov. 15, 2007.
KK. International Patent Application Publication No. WO 2010/138817 A1, Ow-Wing, K., Glucose Monitoring System with Wireless Communications, Dec. 2, 2010; International Patent Application Serial No. WO 2010/138817 A1, filed May 28, 2010.
LL. International Patent Application Publication No. WO 2004/052204 A1, Kim, Kwan-Ho, Blood Glucose Monitoring System, Jun. 24, 2004; International Patent Application Serial No. PCT/KR2003/000398, filed Feb. 28, 2003.

What is claimed is:

1. A central data exchange system for treating a patient with insulin, comprising:
a communication system comprising a communications interface, a hub device, a plurality of glucose measurement devices, a plurality of insulin delivery devices, and a diabetes assistant device, wherein:
one or more of the plurality of glucose measurement devices are configured to measure glucose of the patient;
one or more of the plurality of insulin delivery devices are configured to deliver a dosage of insulin to the patient;
the hub device is configured for implementing inter-device connection between the diabetes assistant device and the plurality of glucose measurement devices and the plurality of insulin delivery devices, wherein the hub device is configured to receive input data from one or more of the plurality of glucose measurement devices and one or more of the plurality of insulin delivery devices and transmit the input data to the diabetes assistant device, the input data comprising glucose measurements or insulin delivery data;
the diabetes assistant device comprises a processor and a non-volatile memory, the non-volatile memory comprising program instructions configured to cause the processor to:
receive the input data transmitted from the hub device;
classify the input data based on a type of glucose measurement device performing the glucose measurement;
assign a risk value to at least one glucose measurement within the input data following a data transformation that addresses asymmetry of glucose measurements;
generate output advisory messages based on the assigned risk values, the output advisory messages including one or more of insulin dosage information specific to the patient, patient alerts, and control signals for one or more of the plurality of glucose measurement devices or one or more of the plurality of insulin delivery devices;
record the classification of input data, the assignment of risk values, and the output advisory messages as patient status data; and
transmit, via the communications interface, the patient status data to a central data exchange node; and
the communications interface is configured to establish a one-way connection that is from the diabetes assistance device to the central data exchange node.

2. The system recited in claim 1, wherein the plurality of glucose measurement devices comprises a self-monitoring blood glucose (SMBG) device and a continuous glucose monitoring (CGM) device.

3. The system recited in claim 1, wherein the plurality of insulin delivery devices comprises a multiple daily insulin injection pump and a continuous subcutaneous insulin injection pump.

4. The system recited in claim 1, wherein the program instructions are configured to cause the processor to classify the input data as one or more of SMBG data, SMBG plus insulin pump data, CGM data, or CGM plus insulin pump data.

5. The system recited in claim 1, and wherein
the communication system further comprises a heart rate sensor, wherein the hub device is configured for implementing inter-device connection between the diabetes assistant device and the heart rate sensor, wherein the hub device is configured to receive heart rate sensor data as part of the input data.

6. The system recited in claim 1, and wherein
the communication system further comprises a blood pressure sensor, wherein the hub device is configured for implementing inter-device connection between the diabetes assistant device and the blood pressure sensor, wherein the hub device is configured to receive blood pressure sensor data as part of the input data.

7. The system recited in claim 1, and wherein
the communication system further comprises an accelerometer, wherein the hub device is configured for implementing inter-device connection between the diabetes assistant device and the accelerometer, wherein the hub device is configured to receive accelerometer data as part of the input data.

8. The system recited in claim 1, and wherein
the communication system further comprises an electrocardiogram sensor, wherein the hub device is configured for implementing inter-device connection between the diabetes assistant device and the electrocardiogram, wherein the hub device is configured to receive electrocardiogram data as part of the input data.

9. The system recited in claim 1, wherein the central data exchange system is configured for treating a plurality of patients and the communication system comprises a plurality of hub devices and a plurality of diabetes assistant devices.

10. The system recited in claim 1, wherein said central data exchange node comprises a server.

11. The system recited in claim 1, wherein the program instructions are configured to cause the processor to transmit the patient status data to a health care provider.

12. The system recited claim 1, wherein the program instructions are configured to cause the processor to transmit the patient status data to an emergency responder.

13. The system recited in claim 1, wherein the program instructions are configured to cause the processor to transmit the patient status data to a health care organization.

14. The system recited in claim 3, wherein the program instructions are configured to cause the processor to analyze data from at least one of said insulin injection pumps and to determine an operational state of said pump from said data analysis.

15. The system recited in claim 1, wherein said diabetes assistant device is a cell phone.

16. The system recited in claim 1, wherein said diabetes assistant device is a tablet computer.

17. The system recited claim 1, wherein the program instructions are configured to cause the processor to implement a closed loop control of delivery of insulin from the one or more of the plurality of insulin delivery devices based on the risk value of at least one glucose measurement.

18. A central data exchange system, comprising:
a communication system comprising a communications interface, a hub device, a plurality of glucose measurement devices, a plurality of insulin delivery devices, a diabetes assistant device, and a central data exchange node, wherein:
one or more of the plurality of glucose measurement devices are configured measure glucose of a patient;
one or more of the plurality of insulin delivery devices are configured to deliver a dosage of insulin to the patient;
the hub device is configured for implementing inter-device connection between the diabetes assistant device and the plurality of glucose measurement devices and the plurality of insulin delivery devices, wherein the hub device is configured to receive input data from one or more of the plurality of glucose measurement devices and one or more of the plurality of insulin delivery devices and transmit the input data to the diabetes assistant device, the input data comprising glucose measurements;
the diabetes assistant device comprises a processor and a non-volatile memory, the non-volatile memory comprising program instructions configured to cause the processor to:
receive the input data transmitted from the hub device;
classify the input data based on a type of glucose measurement device performing the glucose measurement;
assign a risk value to at least one glucose measurement within the input data following a data transformation that addresses asymmetry of glucose measurements;
generate output advisory messages based on the assigned risk values, the output advisory messages including insulin dosage information specific to the patient, patient alerts, and control signals for one or more of the plurality of glucose measurement devices and one or more of the plurality of insulin delivery devices;
record the classification of input data, the assignment of risk values, and the output advisory messages as patient status data; and
transmit, via the communications interface, the patient status data to the central data exchange node; and
the communications interface is configured to establish a one-way connection that is from the diabetes assistance device to the central data exchange node.

19. The system recited in claim 18, wherein said central data exchange node comprises a server.

20. The system recited in claim 18, wherein the plurality of glucose measurement devices comprises a self-monitoring blood glucose (SMBG) device and a continuous glucose monitoring (CGM) device.

21. The system recited in claim 18, wherein the plurality of insulin delivery devices comprises a multiple daily insulin injection pump and a continuous subcutaneous insulin injection pump.

22. The system recited in claim 18, wherein the program instructions are configured to cause the processor to classify the input data as one or more of SMBG data, SMBG plus insulin pump data, CGM data, or CGM plus insulin pump data.

23. The system recited in claim 18, and wherein
the communication system further comprises a heart rate sensor, wherein the hub device is configured for implementing inter-device connection between the diabetes assistant device and the heart rate sensor, wherein the hub device is configured to receive heart rate sensor data as part of the input data.

24. The system recited in claim 18, and wherein
the communication system further comprises a blood pressure sensor, wherein the hub device is configured for implementing inter-device connection between the diabetes assistant device and the blood pressure sensor, wherein the hub device is configured to receive blood pressure sensor data as part of the input data.

25. The system recited in claim 18, and wherein
the communication system further comprises an accelerometer, wherein the hub device is configured for implementing inter-device connection between the diabetes assistant device and the accelerometer, wherein the hub device is configured to receive accelerometer data as part of the input data.

26. The system recited in claim 18, and wherein
the communication system further comprises an electrocardiogram sensor, wherein the hub device is configured for implementing inter-device connection between the diabetes assistant device and the electrocardiogram, wherein the hub device is configured to receive electrocardiogram data as part of the input data.

27. The system recited in claim 18, wherein the central data exchange system is configured for treating a plurality of patients and the communication system comprises a plurality of hub devices and a plurality of diabetes assistant devices.

28. A central data exchange system, comprising:
a communication system comprising a communications interface, a plurality of glucose measurement devices, a plurality of insulin delivery devices, a diabetes assistant device, and a central data exchange node, wherein:
one or more of the plurality of glucose measurement devices are configured measure glucose of a patient;
one or more of the plurality of insulin delivery devices are configured to deliver a dosage of insulin to the patient;
the diabetes assistant device comprises a processor and a non-volatile memory, the non-volatile memory comprising program instructions configured to cause the processor to:
receive input data transmitted from the one or more of the plurality of glucose measurement devices and the one or more of the plurality of insulin delivery devices, the input data comprising glucose measurements;

classify the input data based on a type of glucose measurement device performing the glucose measurement;

assign a risk value to at least one glucose measurement within the input data following a data transformation that addresses asymmetry of glucose measurements;

generate output advisory messages based on the assigned risk values, the output advisory messages including insulin dosage information specific to the patient, patient alerts, and control signals for one or more of the plurality of glucose measurement devices and one or more of the plurality of insulin delivery devices;

record the classification of input data, the assignment of risk values, and the output advisory messages as patient status data; and transmit, via the communications interface, the patient status data to the central data exchange node; and the communications interface is configured to establish a one-way connection that is from the diabetes assistance device to the central data exchange node.

29. The system recited in claim 28, wherein said central data exchange node comprises a server.

30. A central data exchange system for treating a patient with insulin, comprising:

a communication system comprising a communications interface, a hub device, and a diabetes assistant device, wherein:

the hub device is configured for implementing inter-device connection between the diabetes assistant device and a plurality of glucose measurement devices and a plurality of insulin delivery devices, wherein the hub device is configured to receive input data from one or more of the plurality of glucose measurement devices and one or more of the plurality of insulin delivery devices and transmit the input data to the diabetes assistant device, the input data comprising glucose measurements; and the diabetes assistant device comprises a processor and a non-volatile memory, the non-volatile memory comprising program instructions configured to cause the processor to:

receive the input data transmitted from the hub device;

classify the input data based on a type of glucose measurement device performing the glucose measurement;

assign a risk value to at least one glucose measurement within the input data following a data transformation that addresses asymmetry of glucose measurements;

generate output advisory messages based on the assigned risk values, the output advisory messages including insulin dosage information specific to the patient, patient alerts, and control signals for one or more of the plurality of glucose measurement devices and one or more of the plurality of insulin delivery devices;

record the classification of input data, the assignment of risk values, and the output advisory messages as patient status data; and transmit, via the communications interface, the patient status data to a central data exchange node, wherein the communications interface is configured to establish a one-way connection that is from the diabetes assistance device to the central data exchange node.

* * * * *